(12) United States Patent
Nemoto

(10) Patent No.: US 11,998,394 B2
(45) Date of Patent: Jun. 4, 2024

(54) ULTRASOUND IMAGING SYSTEM, OPERATION METHOD OF ULTRASOUND IMAGING SYSTEM, AND COMPUTER-READABLE RECORDING MEDIUM

(71) Applicant: OLYMPUS CORPORATION, Tokyo (JP)

(72) Inventor: Kazuhito Nemoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 153 days.

(21) Appl. No.: 17/397,339

(22) Filed: Aug. 9, 2021

(65) Prior Publication Data

US 2021/0361263 A1 Nov. 25, 2021

Related U.S. Application Data

(63) Continuation of application No. PCT/JP2020/012442, filed on Mar. 19, 2020.

(30) Foreign Application Priority Data

Mar. 19, 2019 (JP) ................. 2019-050869

(51) Int. Cl.
*A61B 8/08* (2006.01)
*A61B 8/14* (2006.01)

(52) U.S. Cl.
CPC .............. *A61B 8/5207* (2013.01); *A61B 8/14* (2013.01)

(58) Field of Classification Search
None
See application file for complete search history.

(56) References Cited

U.S. PATENT DOCUMENTS 5,905,527 A 5/1999 Inou et al.
6,312,385 B1 * 11/2001 Mo .................. G06T 7/136
600/443

(Continued)

FOREIGN PATENT DOCUMENTS

JP S61-201588 A 9/1986
JP H06-203164 A 7/1994

(Continued)

OTHER PUBLICATIONS

International Search Report dated Jun. 9, 2020 received in PCT/JP2020/012442.

(Continued)

*Primary Examiner* — Joel Lamprecht
*Assistant Examiner* — Ashish S Jasani
(74) *Attorney, Agent, or Firm* — Scully, Scott, Murphy & Presser, P.C.

(57) ABSTRACT

An ultrasound imaging system includes a processor configured to: generate, based on an ultrasound signal acquired through ultrasound transmission and reception to and from an observation target by an ultrasound transducer, plural ultrasound images chronologically; calculate a correlation value in each of ultrasound images that are chronologically consecutive, for each of plural areas set in each of the ultrasound images; calculate contrasts based on correlation values calculated for the plural areas; calculate a spatial distribution of the contrasts in each of the ultrasound images; and select an ultrasound image based on the contrasts and the spatial distribution of the contrasts.

11 Claims, 8 Drawing Sheets

(56) References Cited

U.S. PATENT DOCUMENTS

2013/0204135 A1* 8/2013 Kucewicz ................ G06T 5/00
  600/443
2015/0327838 A1* 11/2015 Francis ................ A61B 8/4433
  600/459
2019/0357878 A1 11/2019 Nemoto

FOREIGN PATENT DOCUMENTS

| JP | 2011-217826 A | 11/2011 |
| JP | 2015-131100 A | 7/2015 |
| JP | 2016-149073 A | 8/2016 |
| WO | 2018/163827 A1 | 9/2018 |

OTHER PUBLICATIONS

Chinese Office Action dated Feb. 29, 2024 received in 202080020651.0.

* cited by examiner

ULTRASOUND IMAGING SYSTEM, OPERATION METHOD OF ULTRASOUND IMAGING SYSTEM, AND COMPUTER-READABLE RECORDING MEDIUM

CROSS-REFERENCE TO RELATED APPLICATION

This application is a continuation of International Application No. PCT/JP2020/012442, filed on Mar. 19, 2020, the entire contents of which are incorporated herein by reference.

BACKGROUND

1. Technical Field

The present disclosure relates to an ultrasound imaging system, an operation method of the ultrasound imaging system, and a computer-readable recording medium.

2. Related Art

In the related art, ultrasound imaging systems are used in the medical field. These ultrasound imaging systems generate, on the basis of ultrasound signals, ultrasound images that are scanned images of cross sections of subjects. Ultrasound signals are acquired through ultrasound transmission and reception to and from an observation target by an ultrasound transducer arranged at a distal end of an insertion unit inserted into the subject. A known ultrasound imaging system has a freezing function for a user to specify and display an image of a desired time point while a display device is displaying subject images live. Furthermore, another known ultrasound imaging system has a prefreezing function for constantly storing subject images temporarily for a certain time period and selecting a freeze image from the temporarily stored images at a time point when a user turns on a freezing switch, the freeze image being an image having little blurring due to relative movement.

Ultrasound imaging systems for selecting freeze images on the basis of movement information in ultrasound images have been known as technical means for selecting images with less movement using the prefreezing function (see, for example, Japanese Patent Application Laid-open No. 2015-131100).

SUMMARY

In some embodiments, an ultrasound imaging system includes a processor configured to: generate, based on an ultrasound signal acquired through ultrasound transmission and reception to and from an observation target by an ultrasound transducer, plural ultrasound images chronologically; calculate a correlation value in each of ultrasound images that are chronologically consecutive, for each of plural areas set in each of the ultrasound images; calculate contrasts based on correlation values calculated for the plural areas; calculate a spatial distribution of the contrasts in each of the ultrasound images; and select an ultrasound image based on the contrasts and the spatial distribution of the contrasts.

In some embodiments, provided is an operation method of an ultrasound imaging system. The operation method includes: generating, based on an ultrasound signal acquired through ultrasound transmission and reception to and from an observation target by an ultrasound transducer, plural ultrasound images chronologically; calculating a correlation value in each of ultrasound images that are chronologically consecutive, for each of plural areas set in each of the ultrasound images; calculating contrasts based on the correlation values calculated for the plural areas; calculating a spatial distribution of the contrasts in each of the ultrasound images; and selecting an ultrasound image based on the contrasts and the spatial distribution of the contrasts.

In some embodiments, provided is a non-transitory computer-readable recording medium with an executable program stored thereon. The program is an operation program for an ultrasound imaging system. The operation program causes a processor of the ultrasound imaging system to execute: generating, based on an ultrasound signal acquired through ultrasound transmission and reception to and from an observation target by an ultrasound transducer, plural ultrasound images chronologically; calculating a correlation value in each of ultrasound images that are chronologically consecutive, for each of plural areas set in each of the ultrasound images; calculating contrasts based on of the correlation values calculated for the plural areas; calculating a spatial distribution of the contrasts in each of the ultrasound images; and selecting an ultrasound image based on the contrasts and the spatial distribution of the contrasts.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasound imaging system, an operation method of the ultrasound imaging system, and an operation program for the ultrasound imaging system, according to the disclosure, will be described below by reference to the drawings. The disclosure is not limited by these embodiments. The disclosure is applicable generally to ultrasound imaging systems, operation methods for the ultrasound imaging systems, and operation programs for the ultrasound imaging systems.

Any elements that are the same or corresponding to each other are assigned with the same reference sign throughout the drawings, as appropriate. It also needs to be noted that the drawings are schematic, and relations between dimensions of each element therein and proportions between the elements therein may be different from the actual ones. The drawings may also include a portion that differs in its dimensional relations or proportions between the drawings.

EMBODIMENTS

Figure 1:
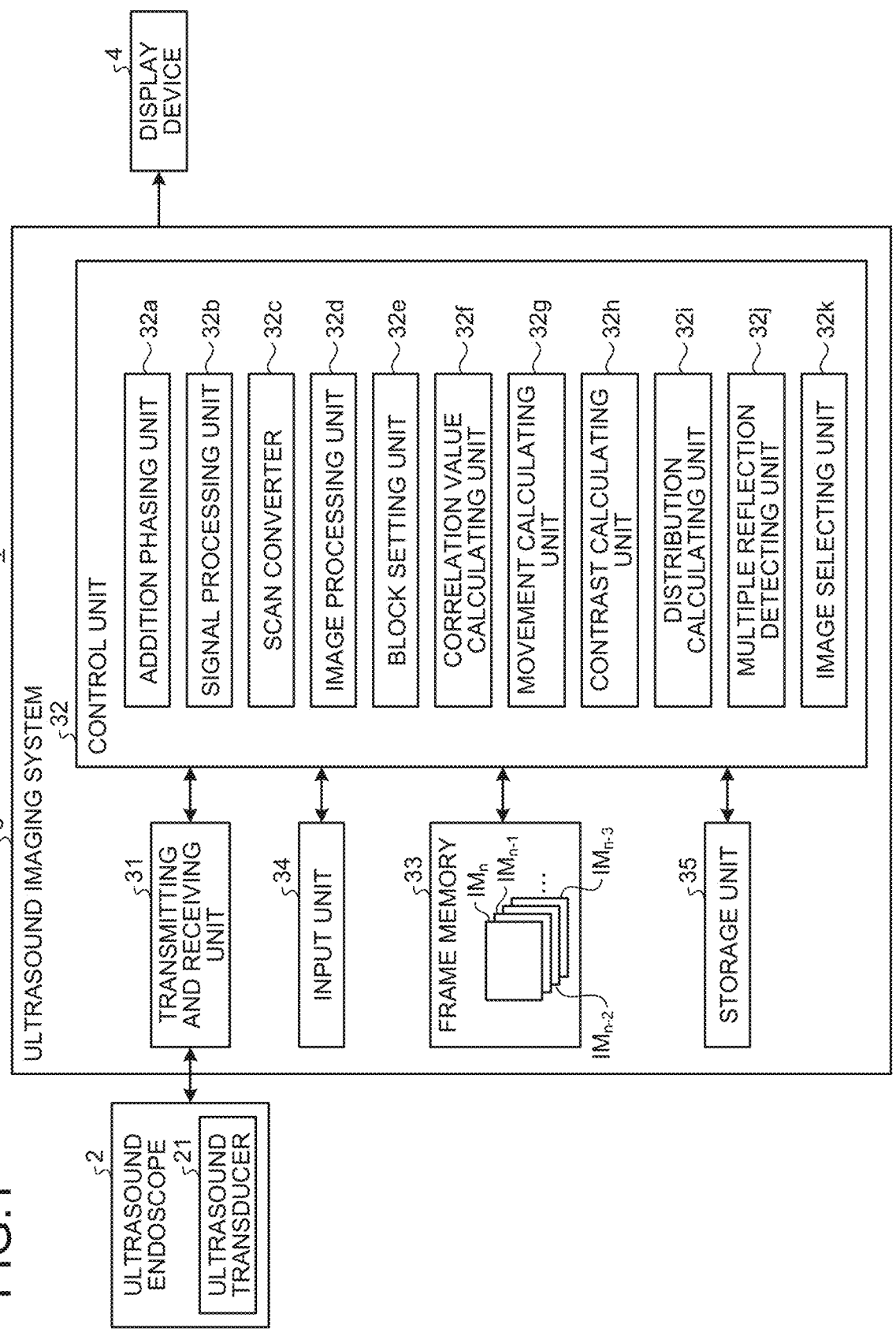
FIG. 1 is a block diagram illustrating a configuration of an ultrasound diagnosis system including an ultrasound imaging system according to a first embodiment of the disclosure.

FIG. 1 is a block diagram illustrating a configuration of an ultrasound diagnosis system including an ultrasound imaging system according to a first embodiment of the disclosure. An ultrasound diagnosis system 1 illustrated in FIG. 1 includes: an ultrasound endoscope 2 that transmits ultrasound to a subject, which is an observation target, and that receives the ultrasound reflected by the subject; an ultrasound imaging system 3 that generates an ultrasound image on the basis of an ultrasound signal acquired by the ultrasound endoscope 2; and a display device 4 that displays the ultrasound image generated by the ultrasound imaging system 3.

The ultrasound endoscope 2 has, at a distal end portion thereof, an ultrasound transducer 21 that: converts an electric pulse signal received from the ultrasound imaging system 3, into ultrasound pulses (acoustic pulses); emits the ultrasound pulses to the subject; converts ultrasound echoes reflected by the subject, into an electric echo signal representing the ultrasound echoes by change in voltage; and outputs the electric echo signal. The ultrasound transducer 21 is arranged at a distal end of an insertion unit inserted into the subject. The ultrasound transducer 21 is a radial ultrasound transducer having a scan surface arranged along an insertion direction of the insertion unit of an endoscope thereof, but may be a convex ultrasound transducer or a linear ultrasound transducer, instead. Furthermore, the ultrasound endoscope 2 may be configured such that: the ultrasound transducer 21 performs scanning mechanically; or plural elements are provided in an array as the ultrasound transducer 21 and perform electronic scanning by electronically changing the elements involved in transmission and reception or inserting delay in transmission and reception by the elements.

The ultrasound endoscope 2: usually has an imaging optical system and an imaging element; is inserted in the gastrointestinal tract (the esophagus, the stomach, the duodenum, and the large intestine) or the respiratory organs (the trachea and the bronchus) of a subject; and is able to capture images of the gastrointestinal tract or respiratory organs, and the organs surrounding the gastrointestinal tract or respiratory organs (the pancreas, the gallbladder, the bile duct, the biliary tract, the lymph nodes, the mediastinal organ, and/or the blood vessels, for example). The ultrasound endoscope 2 also has a light guide that guides illumination light to be emitted to the subject at the time of imaging. This light guide has: a distal end portion that reaches the distal end of the insertion unit to be inserted into the subject, the insertion unit being that of the ultrasound endoscope 2; and a proximal end portion connected to a light source device that generates the illumination light.

The ultrasound imaging system 3 chronologically generates plural ultrasound images on the basis of ultrasound signals acquired through ultrasound transmission and reception to and from an observation target by the ultrasound transducer 21. The ultrasound imaging system 3 includes a transmitting and receiving unit 31, a control unit (a processor) 32, a frame memory 33, an input unit 34, and a storage unit 35.

The transmitting and receiving unit 31: is electrically connected to the ultrasound endoscope 2; transmits, on the basis of a predetermined waveform and transmission timing, a transmission signal (a pulse signal) formed of high voltage pulses, to the ultrasound transducer 21; and receives an echo signal that is an electric reception signal, from the ultrasound transducer 21.

A frequency band of the pulse signal transmitted by the transmitting and receiving unit 31 is preferably a wide band substantially covering a linear response frequency band for electric-acoustic conversion of the pulse signal by the ultrasound transducer 21 into ultrasound pulses.

The transmitting and receiving unit 31 has functions of transmitting various control signals output by the control unit 32 to the ultrasound endoscope 2, and receiving various types of information including an ID for identification from the ultrasound endoscope 2 and transmitting the various types of information to the control unit 32.

The control unit (the processor) 32 controls the overall ultrasound diagnosis system 1. The control unit 32 is implemented using, for example, a central processing unit (CPU) and/or various arithmetic circuits that has/have arithmetic and control functions. The control unit 32 integrally controls the ultrasound imaging system 3 by reading information recorded and stored in the storage unit 35 from the storage unit 35 and executing various types of arithmetic processing related to an operation method of the ultrasound imaging system 3.

The control unit (the processor) 32 has an addition phasing unit 32a, a signal processing unit 32b, a scan converter 32c, an image processing unit 32d, a block setting unit 32e, a correlation value calculating unit 32f, a movement calculating unit 32g, a contrast calculating unit 32h, a distribution calculating unit 32i, a multiple reflection detecting unit 32j, and an image selecting unit 32k. However, any of the control unit 32 and the addition phasing unit 32a to the image selecting unit 32k may be configured using another CPU, for example.

The addition phasing unit 32a receives an echo signal from the transmitting and receiving unit 31 and generates and outputs data (hereinafter, referred to as RF data) on a digital radio frequency (RF) signal. The addition phasing unit 32a: performs sensitivity time control (STC) correction in which amplification is performed with a higher amplification factor for an echo signal larger in reception depth; performs processing, such as filtering, on the amplified echo signal; thereafter generates RF data in the time domain by A/D conversion of the amplified echo signal processed; and outputs the generated RF data, to the signal processing unit 32b. If the ultrasound endoscope 2 has a configuration in which the ultrasound transducer 21 having plural elements provided in an array is caused to perform electronic scanning, the addition phasing unit 32a has a multi-channel circuit for beam combination corresponding to the plural elements.

The signal processing unit 32b generates digital B mode reception data on the basis of the RF data received from the transmitting and receiving unit 31. The signal processing unit 32b performs known processing, such as bandpass filtering, envelope demodulation, and logarithmic transformation, on the RF data, and generates the digital B-mode reception data. In the logarithmic transformation, a common logarithm of a quantity resulting from division of the RF data by a reference voltage Vc is expressed as a decibel value. The signal processing unit 32b outputs the generated B-mode reception data, to the image processing unit 32d.

The scan converter 32c converts the scan direction of the B-mode reception data received from the signal processing unit 32b to generate frame data. Specifically, the scan converter 32c converts the scan direction of the B-mode reception data into a display direction of the display device 4 from the ultrasound scan direction.

The image processing unit 32d generates B-mode image data (hereinafter, simply referred to as image data also) including an ultrasound image that is a B-mode image for display by conversion of the amplitude of the echo signal into luminance. The image processing unit 32d generates the B-mode image data by performing signal processing using known techniques such as gain processing and contrast processing on the frame data from the scan converter 32c, and performing, for example, thinning of data according to a data step width determined according to an image display range in the display device 4. A B-mode image is a gray scale image in which red (R), green (G), and blue (B) values have been made to match one another, the R, G, and B values corresponding to variables in the case where the RGB colorimetric system is adopted as a color space.

After performing coordinate transformation in which the B-mode reception data from the signal processing unit 32b are rearranged so as to enable correct spatial representation of the scan range, the image processing unit 32d fills in gaps among the B-mode reception data by performing interpolation processing among the B-mode reception data to generate the B-mode image data.

Figure 2:
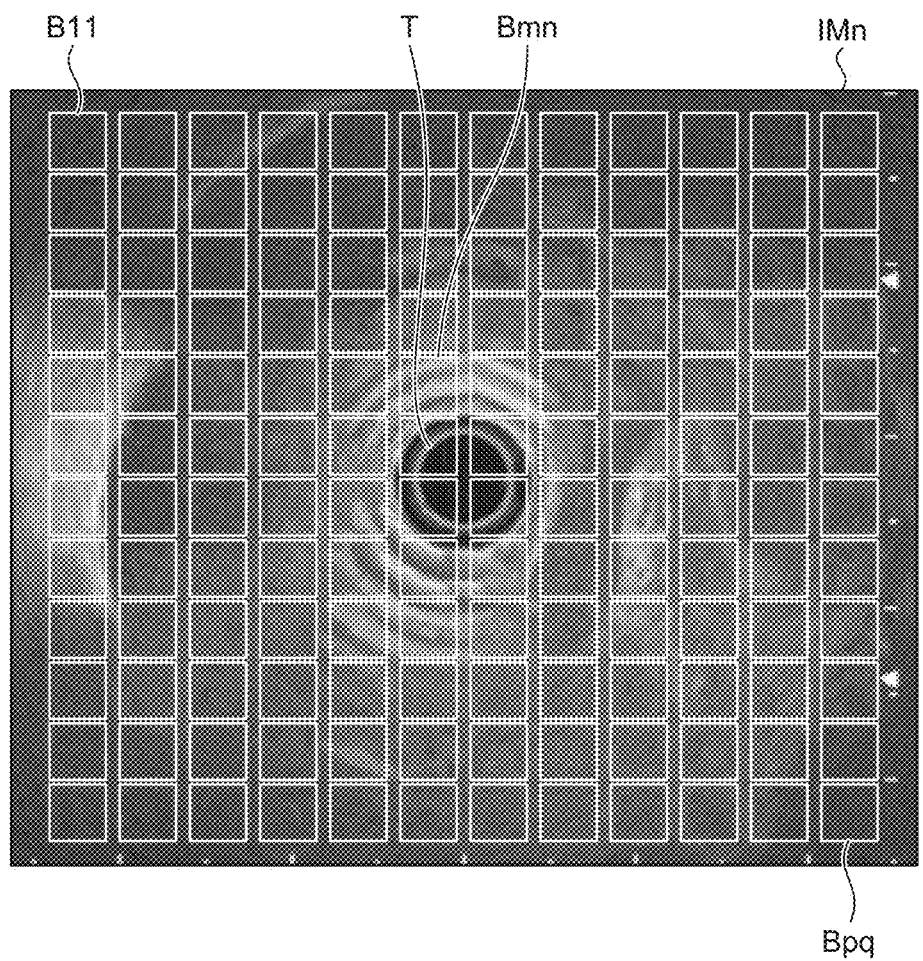
FIG. 2 is a diagram illustrating measurement areas (blocks) set in an image for calculation of correlation values.

FIG. 2 is a diagram illustrating measurement areas (blocks) set in an image for calculation of correlation values. As illustrated in FIG. 2, the block setting unit 32e sets vertically p×horizontally q (where p and q are natural numbers equal to or larger than 2) blocks from a block B11 to a block Bpq in a lattice form on an ultrasound image $IM_n$ that is the latest ultrasound image. A transducer area T corresponding to the ultrasound transducer 21 displayed in the ultrasound image is included in the approximate center of FIG. 2. An example where the ultrasound transducer 21 of the radial type having the transducer area T positioned in the center of the ultrasound image is used is described herein, but the ultrasound transducer 21 may be of the convex type or the linear type instead.

The correlation value calculating unit 32f calculates a correlation value using block matching in each of ultrasound images that are chronologically consecutive (hereinafter, referred to as being chronologically adjacent to each other, for example, in this embodiment), for each of plural areas set in each ultrasound image. Specifically, the correlation value calculating unit 32f calculates, for example, a sum of absolute differences (SAD) value for the pixel values by using block matching, the SAD value being one type of correlation values.

Figure 3:
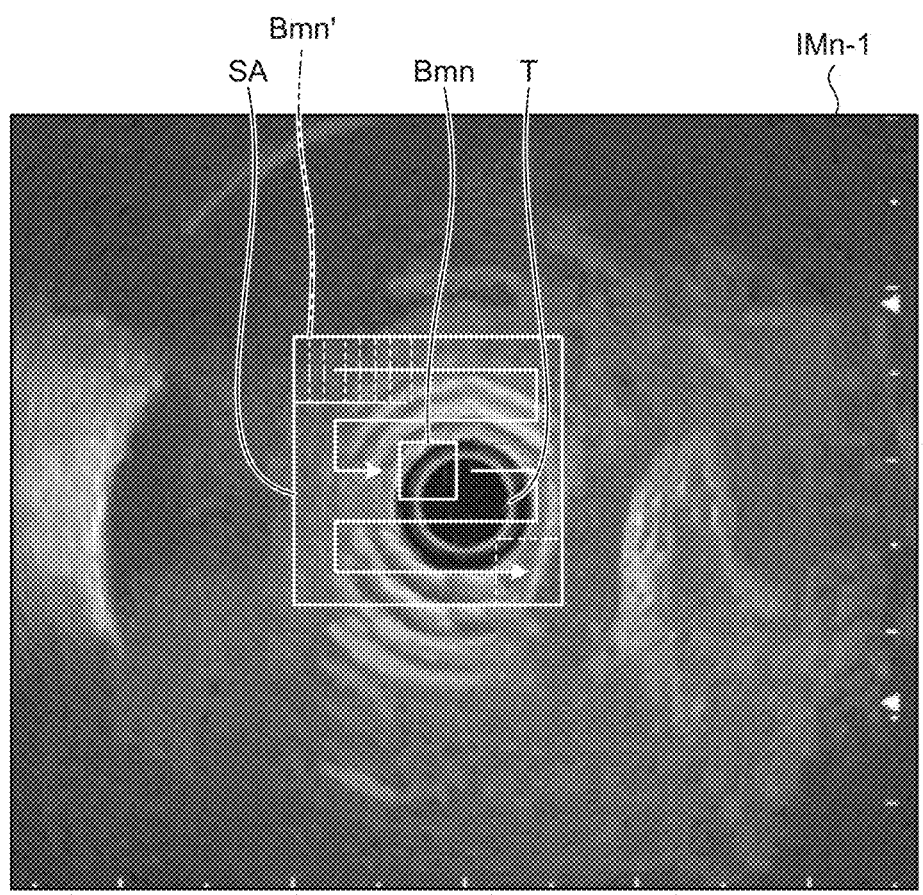
FIG. 3 is a diagram illustrating how the correlation values are calculated.

FIG. 3 is a diagram illustrating how correlation values are calculated. FIG. 3 is a diagram illustrating how an amount of movement of a block Bmn in FIG. 2 is calculated. As illustrated in FIG. 3, the correlation value calculating unit 32f sequentially sets a block Bmn' at plural positions that are calculation positions for correlation values along arrows illustrated in FIG. 3, the block Bmn' being at the same position as a block Bmn set in the ultrasound image $IM_n$, the block Bmn' being included in a search area SA set around a block Bmn set in an ultrasound image $IM_{n-1}$ that is immediately before the ultrasound image $IM_n$, and sequentially calculates correlation values SAD indicating similarities between the blocks Bmn' set in the ultrasound image $IM_{n-1}$ and the block Bmn set in the ultrasound image $IM_n$. Although the sum of squared differences is used herein as a correlation value in block matching, any other correlation value (for example, the sum of squared differences (SSD)) may be used instead.

The movement calculating unit 32g calculates, on the basis of the correlation values SAD, an amount of movement that is an amount by which a subject has moved between ultrasound images that are chronologically consecutive (adjacent). Specifically, the movement calculating unit 32g calculates an amount of movement that is an amount by which a subject captured in the ultrasound image $IM_n$ of the latest frame of plural ultrasound images stored in the frame memory 33 has moved relatively to the subject captured in an ultrasound image that is a frame in the past. When the movement calculating unit 32g has calculated the correlation values SAD of the blocks at all of the calculation positions included in the search area SA, the movement calculating unit 32g calculates an amount of movement that is a vector from the center of the block Bmn to the center of a block having the smallest correlation value SAD. The movement calculating unit 32g repeats this calculation of the amount of movement for each block, and calculates amounts of movement for all of the blocks in the ultrasound image $IM_n$. Lastly, the movement calculating unit 32g calculates an amount of frame movement indicating movement of the whole image from a statistical value (the mean value or the mode, for example) of the amounts of movement of the plural blocks.

The contrast calculating unit 32h calculates a contrast related to the correlation values SAD for each block Bmn. A contrast herein refers to a ratio between the largest value and the smallest value of the correlation values SAD in a predetermined range of the search area SA described above (although any one of other definitions of contrast may be used instead). Specifically, the contrast calculating unit 32h calculates, as a contrast, a ratio between the largest value and the smallest value of the correlation values SAD in a predetermined range around the calculation position with the smallest correlation value SAD (for example, in a range including calculation positions up to those that are away upward, downward, leftward, and rightward from the calculation position with the smallest correlation value SAD by five calculation positions each) in the search area SA. The contrast calculating unit 32h may change the size of the predetermined range for which a contrast is calculated, according to the range of an ultrasound image. For example, the contrast calculating unit 32h may set the predetermined range small if the range of the ultrasound image is large (a wide range has been imaged). This is because multiple reflection described later becomes finely patterned when the range is large.

The distribution calculating unit 32i calculates a contrast distribution in each ultrasound image. Specifically, the distribution calculating unit 32i associates a contrast value of each block calculated by the contrast calculating unit 32h with a position in the ultrasound image $IM_n$.

On the basis of the contrast distribution calculated by the distribution calculating unit 32i, the multiple reflection detecting unit 32j detects a multiple-reflection area. A multiple-reflection area is an area in which a pattern of high and low luminance as seen around the transducer area T in FIG. 2 appears in an ultrasound image, due to influence of a highly reflecting body, such as a sheath of the ultrasound transducer 21. The multiple reflection detecting unit 32j detects, as a multiple-reflection area, an area continuously formed around the transducer area T, the area being formed of areas each having a contrast larger than a threshold. The threshold is, for example, the mean value of the contrasts in the ultrasound image, but may be a statistical value, such as the median or the mode, or may be a preset value or a value set by a user.

The image selecting unit 32k selects an ultrasound image on the basis of contrasts and a contrast distribution. Specifically, the image selecting unit 32k selects an ultrasound image on the basis of a size of a multiple-reflection area detected by the multiple reflection detecting unit 32j. The image selecting unit 32k may select an ultrasound image on the basis of contrasts, a contrast distribution, and an amount of movement. When the image selecting unit 32k receives input of a freeze instruction signal, the image selecting unit 32k selects an ultrasound image on the basis of contrasts and a contrast distribution.

The frame memory 33 is implemented using, for example, a ring buffer, and chronologically stores therein a certain amount of ultrasound images (a predetermined number of frames N) generated by the image processing unit 32d. When the capacity becomes insufficient (when a predetermined number of frames of B-mode image data have been stored), the predetermined number of frames of the latest ultrasound images are stored in chronological order by the oldest B-mode image data being overwritten by the latest B-mode image data. As illustrated in FIG. 1, the frame memory 33 stores therein plural ultrasound images ($IM_{n-1}$, $IM_{n-2}$, $IM_{n-3}$, ... ) that are within the predetermined number of frames from the ultrasound image $IM_n$ of the n-th frame (where n is a natural number equal to or larger than 2) that is the latest ultrasound image. The frame memory 33 also stores correlation values calculated by the correlation value calculating unit 32f, amounts of movement calculated by the movement calculating unit 32g, contrasts calculated by the contrast calculating unit 32h, and contrast distributions calculated by the distribution calculating unit 32i, in association with ultrasound images.

The input unit 34 is implemented using a user interface, such as a keyboard, a mouse, or a touch panel, and receives input of various types of information. The input unit 34 receives input of a freeze instruction signal that is input of an instruction to cause the display device 4 to display a freeze image by means of the prefreezing function.

The storage unit 35 stores therein various programs including an operation program for executing the operation method of the ultrasound imaging system 3. The operation program may also be widely distributed by being recorded in a computer readable recording medium, such as a hard disk, a flash memory, a CD-ROM, a DVD-ROM, or a flexible disk. The above described various programs may be acquired by being downloaded via a communication network. The communication network referred to herein is implemented by, for example, any existing public network, a local area network (LAN), or a wide area network (WAN), and may be wired or wireless.

The storage unit 35 having the above described configuration is implemented using, for example, a read only memory (ROM) having, for example, the various programs preinstalled therein, and a random access memory (RAM) storing, for example, arithmetic parameters and data for processing.

Figure 4:
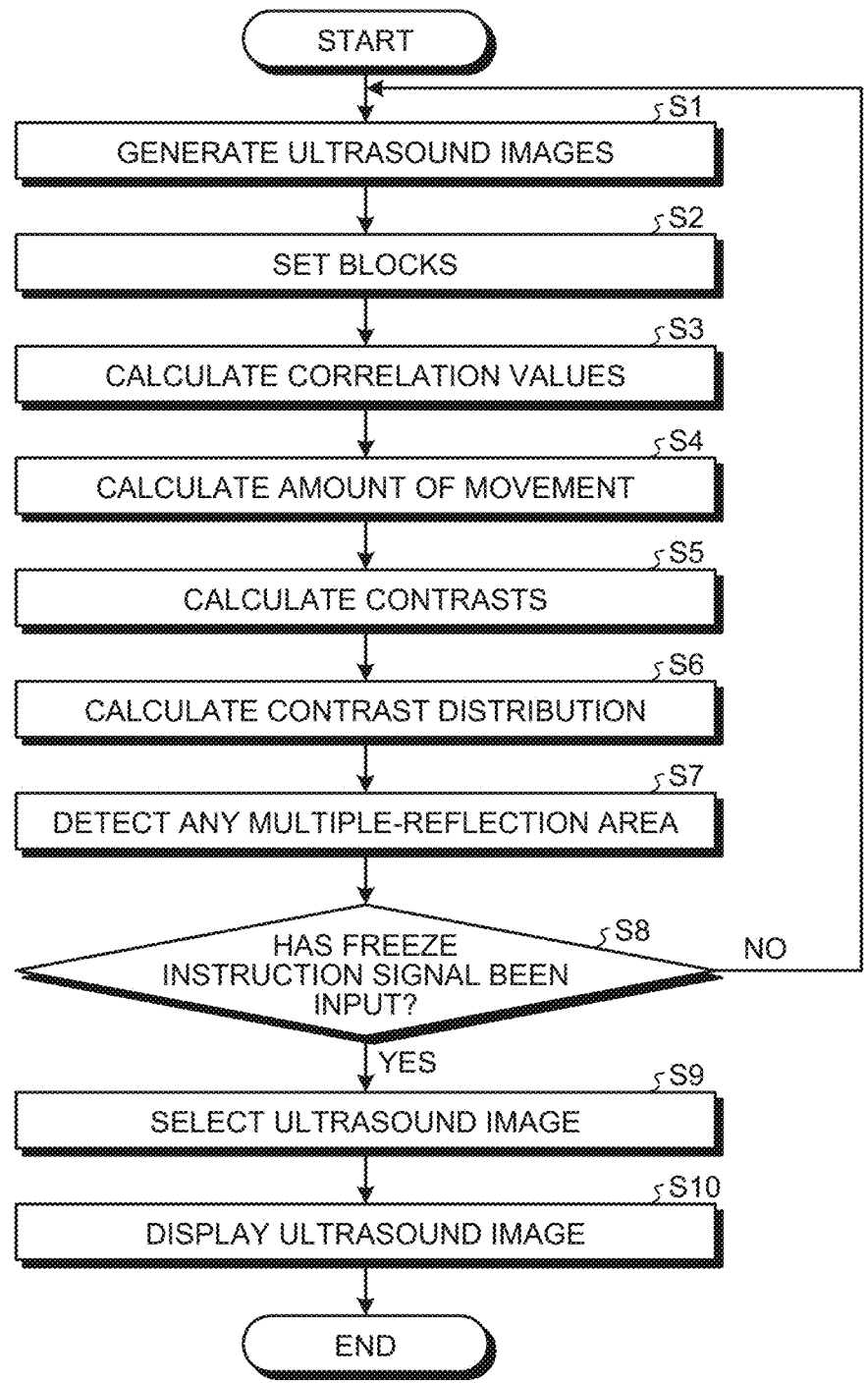
FIG. 4 is a flowchart illustrating an outline of a process in which the ultrasound imaging system selects an ultrasound image.

A process in which the ultrasound diagnosis system 1 selects an ultrasound image will be described next. FIG. 4 is a flowchart illustrating an outline of a process in which an ultrasound imaging system selects an ultrasound image. As illustrated in FIG. 4, the addition phasing unit 32a, the signal processing unit 32b, the scan converter 32c, and the image processing unit 32d execute predetermined signal processing on an echo signal output by the ultrasound endoscope 2 and received by the transmitting and receiving unit 31, to generate an ultrasound image $IM_n$ (Step S1).

Subsequently, the block setting unit 32e sets lattice-like blocks in the ultrasound image $IM_n$ (Step S2).

The correlation value calculating unit 32f then calculates correlation values SAD of the blocks set in the ultrasound image $IM_n$ (Step S3).

The movement calculating unit 32g calculates, on the basis of the correlation values SAD, an amount of movement between adjacent ultrasound images (Step S4).

Figure 5:
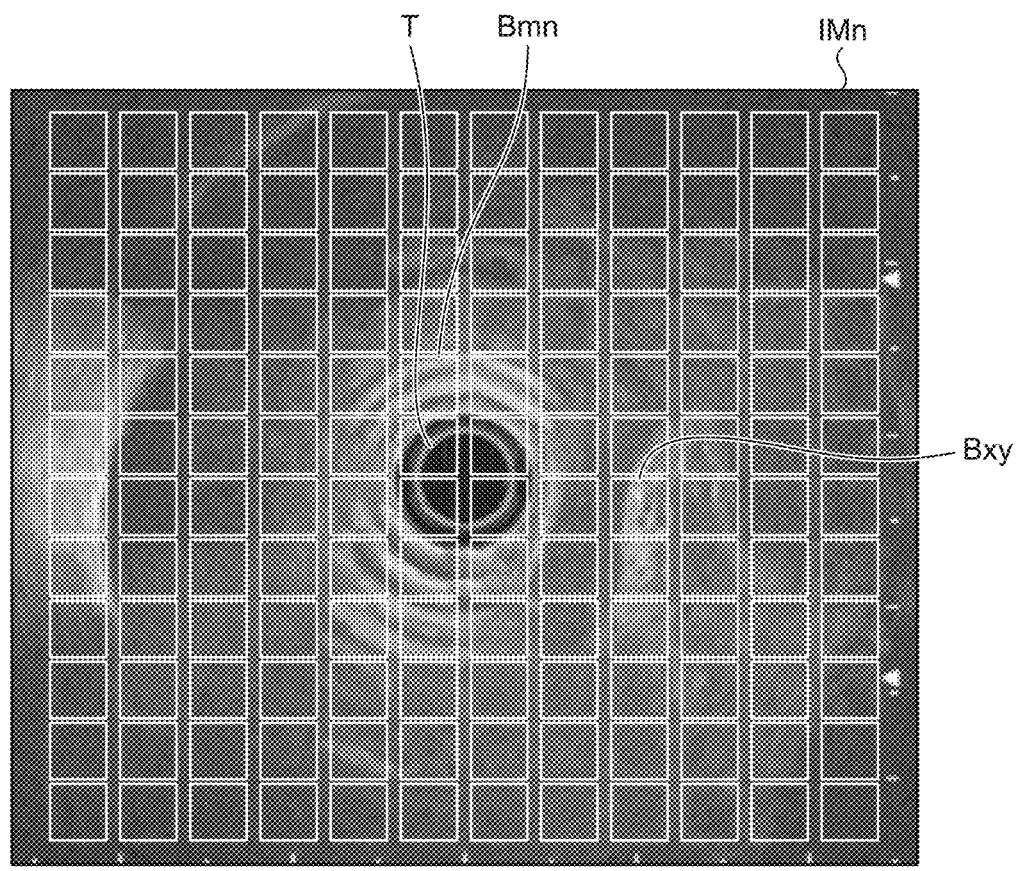
FIG. 5 is a diagram illustrating an example of blocks set in an ultrasound image.

The contrast calculating unit 32h calculates contrasts related to the correlation values SAD (Step 35). FIG. 5 is a diagram illustrating an example of blocks set in an ultrasound image. A contrast between a block Bmn and a block Bxy set in an ultrasound image $IM_n$ illustrated in FIG. 5 will be described below.

Figure 6:
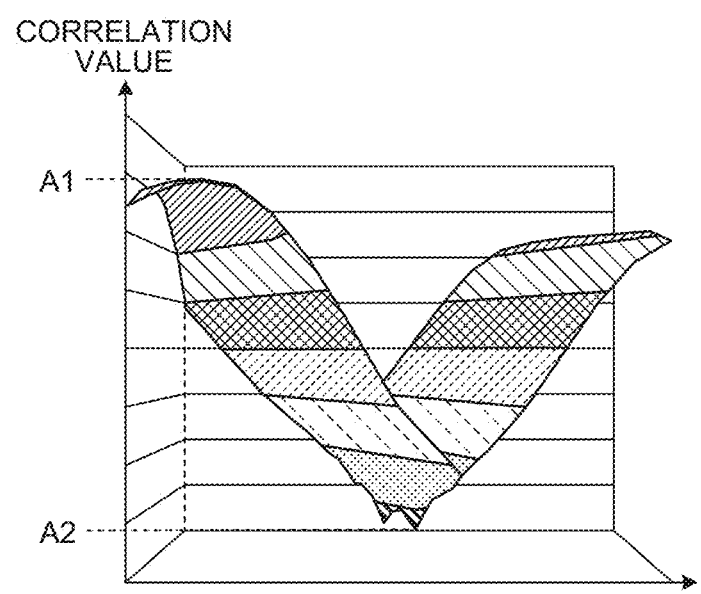
FIG. 6 is a diagram illustrating a correlation value distribution around a calculation position of the smallest correlation value for a block Bmn illustrated in FIG. 5.

The block Bmn is an area strongly affected by multiple reflection, the area having, successively and periodically around a transducer area T, white parts high in luminance and black parts low in luminance. FIG. 6 is a diagram illustrating a correlation value distribution around a calculation position of the smallest correlation value for the block Bmn illustrated in FIG. 5. The higher the similarity between areas, the smaller the correlation value SAD illustrated in FIG. 6 becomes. For the block Bmn, the correlation value drastically increases as the distance from the calculation position of the smallest correlation value increases, due to the influence of multiple reflection. As a result, for the block Bmn, the contrast=the largest value A1/the smallest value A2 is large.

Figure 7:
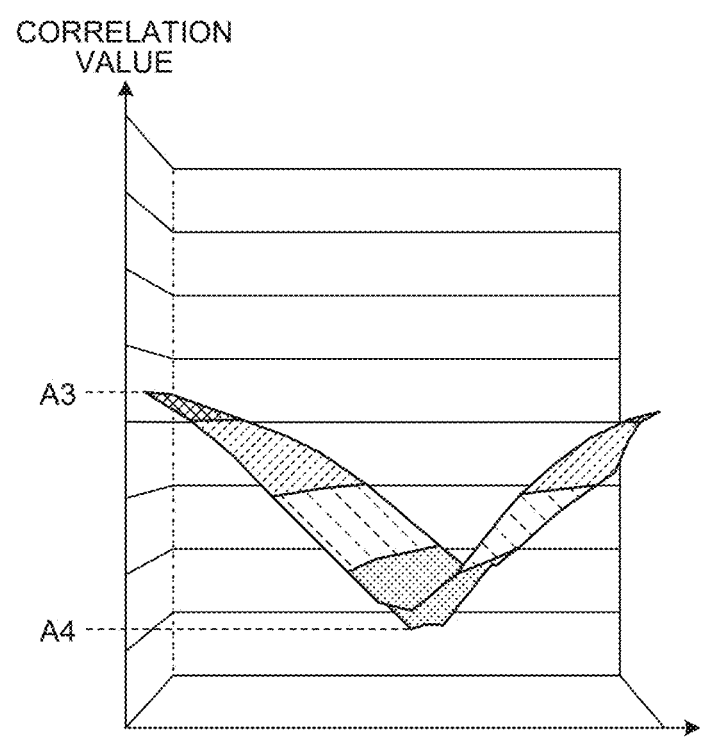
FIG. 7 is a diagram illustrating a correlation value distribution around a calculation position of the smallest correlation value for a block Bxy illustrated in FIG. 5.

In contrast, the block Bxy is an area not affected by multiple reflection. FIG. 7 is a diagram illustrating a correlation value distribution around a calculation position of the smallest correlation value for the block Bxy illustrated in FIG. 5. As illustrated in FIG. 7, for the block Bxy, the correlation value gradually increases as the distance from the calculation position of the smallest correlation value increases. As a result, for the block Bxy, the contrast=the largest value A3/the smallest value A4 is small.

Thereafter, the distribution calculating unit 32i calculates a contrast distribution in the ultrasound image $IM_n$ (Step S6).

Figure 8:
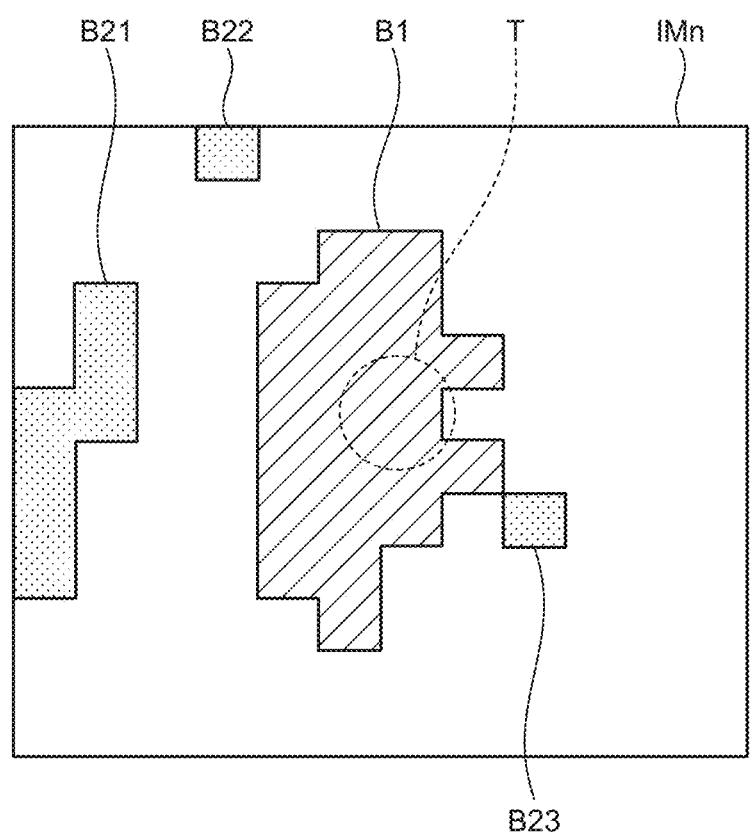
FIG. 8 is a diagram illustrating a multiple-reflection area in the ultrasound image illustrated in FIG. 2.

The multiple reflection detecting unit 32j then detects, on the basis of the contrast distribution calculated by the distribution calculating unit 32i, a multiple-reflection area (Step S7). FIG. 8 is a diagram illustrating a multiple-reflection area in the ultrasound image illustrated in FIG. 2. As illustrated in FIG. 8, the multiple reflection detecting unit 32j detects, as the multiple-reflection area, an area continuously formed around the transducer area T, the area being formed of areas each having a contrast larger than a threshold. Specifically, the multiple reflection detecting unit 32j detects, as the multiple-reflection area, an area B1 continuously formed in four directions, upward, downward, leftward, and rightward, around the transducer area T, the area being formed of areas each having a contrast larger than a threshold. However, the multiple reflection detecting unit 32j does not detect, as the multiple-reflection area, areas B21, B22, and B23 that are not continuous from the transducer area T, even if the areas B21, B22, and B23 have contrasts larger than the threshold. The multiple reflection detecting unit 32j may detect the area B1 and the area B23 as the multiple-reflection area, for being an area continuously formed in eight directions, upward, downward, leftward, rightward, and diagonally, around the transducer area T, the area having contrasts larger than the threshold.

The control unit 32 determines whether or not a freeze instruction signal has been input (Step S8). Specifically, the control unit 32 determines whether or not a predetermined instruction has been input from an input device, the predetermined instruction instructing the input unit 34 to freeze.

If the control unit 32 determines that a freeze instruction signal has not been input (Step S8: No), the process is returned to Step S1 to be continued.

On the contrary, if the control unit 32 determines that a freeze instruction signal has been input (Step S8: Yes), the image selecting unit 32*k* selects an ultrasound image to be displayed by the display device 4 as a freeze image (Step S9). Specifically, the image selecting unit 32*k* selects, as a freeze image, an ultrasound image having a small multiple-reflection area calculated by the multiple reflection detecting unit 32*j* and a small amount of movement calculated by the movement calculating unit 32*g*.

The display device 4 then displays the freeze image on the basis of input from the ultrasound imaging system 3 (Step S10).

As described above, because the image selecting unit 32*k* in the ultrasound imaging system 3 selects an ultrasound image having a small multiple-reflection area, an ultrasound image largely affected by multiple reflection is prevented from being selected as a freeze image. Therefore, the ultrasound imaging system 3 allows users to select images useful for observation highly accurately.

Furthermore, because the image selecting unit 32*k* selects an image having a small amount of movement, an image having a large amount of movement upon imaging of the subject is prevented from being selected as a freeze image.

Being chronologically consecutive means that the two ultrasound images from plural ultrasound images are very close to each other in the chronological display order set for the two ultrasound images (for example, they adjoin each other in the order), and being chronologically adjacent includes, for example, being chronologically near each other with one image or a predetermined number of images between the two ultrasound images (being two ultrasound images away from each other or several ultrasound images away from each other) like the relation between ultrasound images $IM_n$ and $IM_{n-2}$, without being limited to, for example, being chronologically adjacent to each other directly like ultrasound images $IM_n$ and $IM_{n-1}$.

First Modified Example

The image selecting unit 32*k* may select, on the basis of a contrast distribution, an ultrasound image large in contrast in a predetermined area thereof, from ultrasound images. Specifically, on the basis of contrasts and a contrast distribution, the image selecting unit 32*k* selects an ultrasound image including a puncture needle.

Figure 9:
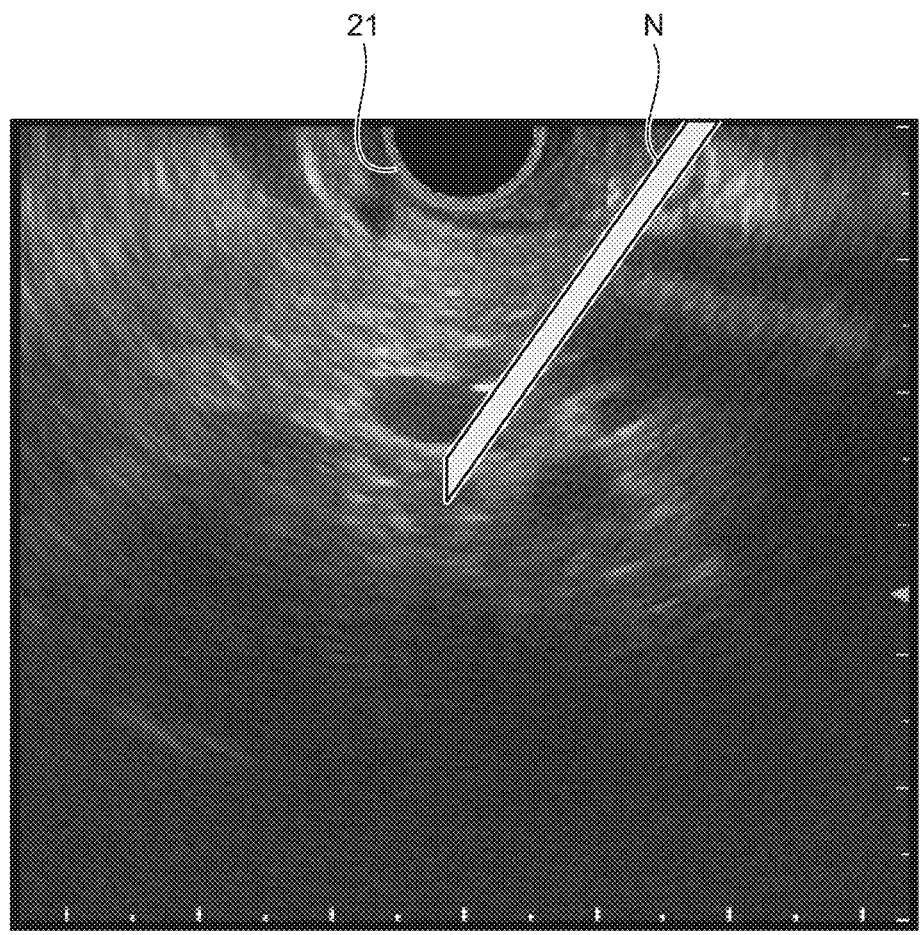
FIG. 9 is a diagram illustrating an ultrasound image including a puncture needle.

FIG. 9 is a diagram illustrating an ultrasound image including a puncture needle. As illustrated in FIG. 9, in a case where the ultrasound endoscope 2 including the convex ultrasound transducer 21 is used, a puncture needle N is captured in an ultrasound image from the direction of the proximal end of the insertion unit of the ultrasound endoscope 2 toward a central part of the ultrasound image. The puncture needle N captured in the ultrasound image corresponds to an area having large luminance. As a result, the periphery of the puncture needle N captured in the ultrasound image is large in contrast related to the correlation values SAD.

The image selecting unit 32*k* selects an image large in contrast near the proximal end of the puncture needle N, that is, at an upper right preset position in the ultrasound image. As a result, the image selecting unit 32*k* is able to select an image including the puncture needle N captured therein and a user is able to selectively view the image including the puncture needle N.

Second Modified Example

The image selecting unit 32*k* may select an ultrasound image excluding any image including a predetermined area or more of a structural object captured therein, the structural object being an object that obstructs observation and being, for example, air. The air captured in the ultrasound image corresponds to an area that is very low in luminance. As a result, the periphery of the air captured in the ultrasound image is large in contrast related to the correlation values. The image selecting unit 32*k* may select an ultrasound image excluding any ultrasound image including a large area of air captured therein, the excluded ultrasound image being an ultrasound image including a predetermined amount or more of an area large in contrast. Furthermore, the image selecting unit 32*k* may exclude any ultrasound image having air captured therein, in consideration of the position of the area large in contrast.

The disclosure enables provision of an ultrasound imaging system, an operation method of the ultrasound imaging system, and an operation program for the ultrasound imaging system that let users select images useful for observation accurately.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound imaging system comprising:
    a processor configured to:
        for each ultrasound image of a plurality of ultrasound images that are chronologically consecutive:
            calculate correlation values for each area of plural areas set in the each ultrasound image, each of the correlation values representing similarities between pixel values of one of a plurality of calculation positions in a previous ultrasound image and pixel values of the each area;
            calculate a ratio of a largest correlation value and a smallest value of the correlation values calculated for the each area of the plural areas as a contrast value for the each area of the plural areas;
            determine a spatial distribution of the contrast values of the plurality of areas in the each ultrasound image; and
            identify a multiple-reflection area in the spatial distribution of the each ultrasound image, the multiple-reflection area including areas of the plurality of areas having a predetermined contrast value; and
        select an ultrasound image from the plurality of ultrasound images having a smallest multiple-reflection area of the multiple-reflection areas of the plurality of ultrasound images.

2. The ultrasound imaging system according to claim 1, wherein the processor is configured to identify, as the multiple-reflection area, an area in the each of the ultrasound images, the area being formed of continuous areas of the plurality of areas, each of the continuous areas having a contrast value larger than a threshold.

3. The ultrasound imaging system according to claim 1, wherein the processor is configured to:
for the each ultrasound image of the plurality of ultrasound images that are chronologically consecutive, calculate, based on the correlation values calculated for the each ultrasound image, an amount of movement that is an amount by which a subject has moved between the each ultrasound image of the plurality of ultrasound images and the previous ultrasound image; and
select the ultrasound image from the plurality of ultrasound images, the ultrasound image selected having the smallest multiple-reflection area and the smallest amount of movement of the plurality of ultrasound images.

4. The ultrasound imaging system according to claim 1, wherein the processor is configured to, in response to receiving input of a freeze instruction signal, select the ultrasound image from the plurality of ultrasound images having the smallest multiple-reflection area.

5. The ultrasound imaging system according to claim 1, wherein the processor is configured to, for the each ultrasound image of the plurality of ultrasound images that are chronologically consecutive, identify, as the multiple-reflection area, areas of the plurality of areas formed around a transducer area and having a predetermined contrast value.

6. An operation method comprising:
for each ultrasound image of a plurality of ultrasound images that are chronologically consecutive:
calculating correlation values for each area of plural areas set in the each ultrasound image, each of the correlation values representing similarities between pixel values of one of a plurality of calculation positions in a previous ultrasound image and pixel values of the each area;
calculating a ratio of a largest correlation value and a smallest value of the correlation values calculated for the each area of the plural areas as a contrast value for the each area of the plural areas;
determining a spatial distribution of the contrast values of the plurality of areas in the each ultrasound image; and
identifying a multiple-reflection area in the spatial distribution of the each ultrasound image, the multiple-reflection area including areas of the plurality of areas having a predetermined contrast value; and
selecting an ultrasound image from the plurality of ultrasound images having a smallest multiple-reflection area of the multiple-reflection areas of the plurality of ultrasound images.

7. A non-transitory computer-readable recording medium with an executable program stored thereon, the executable program causing a computer to at least execute:
for each ultrasound image of a plurality of ultrasound images that are chronologically consecutive:
calculating correlation values for each area of plural areas set in the each ultrasound image, each of the correlation values representing similarities between pixel values of one of a plurality of calculation positions in a previous ultrasound image and pixel values of the each area;
calculating a ratio of a largest correlation value and a smallest value of the correlation values calculated for the each area of the plural areas as a contrast value for the each area of the plural areas;
determining a spatial distribution of the contrast values of the plurality of areas in the each ultrasound image; and
identifying a multiple-reflection area in the spatial distribution of the each ultrasound image, the multiple-reflection area including areas of the plurality of areas having a predetermined contrast value; and
selecting an ultrasound image from the plurality of ultrasound images having a smallest multiple-reflection area of the multiple-reflection areas of the plurality of ultrasound images.

8. The operation method according to claim 6, comprising:
identifying, as the multiple-reflection area, an area in the each of the ultrasound images, the area being formed of continuous areas of the plurality of areas, each of the continuous areas having a contrast value larger than a threshold.

9. The operation method according to claim 6, comprising:
for the each ultrasound image of the plurality of ultrasound images that are chronologically consecutive, calculating, based on the correlation values calculated for the each ultrasound image, an amount of movement that is an amount by which a subject has moved between the each ultrasound image of the plurality of ultrasound images and the previous ultrasound image; and that are chronologically consecutive; and
selecting the ultrasound image from the plurality of ultrasound images, the ultrasound image selected having the smallest multiple-reflection area and the smallest amount of movement of the plurality of ultrasound images.

10. The operation method according to claim 6, comprising:
in response to receiving input of a freeze instruction signal, select the ultrasound image from the plurality of ultrasound images having the smallest multiple-reflection area.

11. The operation method according to claim 6, comprising for the each ultrasound image of the plurality of ultrasound images that are chronologically consecutive, identifying, as the multiple-reflection area, areas of the plurality of areas formed around a transducer area and having a predetermined contrast value.

* * * * *